United States Patent [19]

Smits

[11] Patent Number: 5,354,327
[45] Date of Patent: Oct. 11, 1994

[54] CONDUCTOR COIL WITH SPECIFIC RATIO OF TORQUE TO BENDING STIFFNESS

[75] Inventor: Karel F. A. A. Smits, Oirsbeek, Netherlands

[73] Assignee: Medtronic, Inc., Minneapolis, Minn.

[21] Appl. No.: 43,885

[22] Filed: Apr. 7, 1993

[51] Int. Cl.$^5$ .............................................. A61N 1/05
[52] U.S. Cl. .................................... 607/116; 607/122; 174/117 R
[58] Field of Search ............... 607/116, 119, 122, 123, 607/125–128; 128/642; 604/281, 282; 174/129 R, 133 R, 24, 34, 126.1, 117 R, 117 FF

[56] References Cited

U.S. PATENT DOCUMENTS

| | | | |
|---|---|---|---|
| 3,348,548 | 10/1967 | Chardack . | |
| 3,902,501 | 9/1975 | Citron et al. . | |
| 3,974,834 | 8/1976 | Kane . | |
| 4,106,512 | 8/1978 | Bisping . | |
| 4,463,765 | 8/1984 | Gold . | |
| 4,481,953 | 11/1984 | Gold et al. | 607/127 |
| 4,529,837 | 7/1985 | Borden | 174/129 R |
| 4,667,686 | 5/1987 | Peers-Traverton | 607/127 |
| 5,178,158 | 1/1993 | de Toledo | 604/282 X |

FOREIGN PATENT DOCUMENTS

| | | | |
|---|---|---|---|
| 3215036 | 10/1983 | Fed. Rep. of Germany | 607/119 |
| 9304722 | 3/1993 | World Int. Prop. O. | 604/282 |

OTHER PUBLICATIONS

Kagan–Dixon, Aluminum Round Wire, Flat Wire, Square Wire . . . , 4 Jun. 1969.
John Doring and Robert Flink, "The Impact of Pending Technologies on a Universal Connector Standard", Pace, vol. 9 Nov.–Dec. 1986, Part II pp. 1186–1190.

Primary Examiner—Lee S. Cohen
Assistant Examiner—Jeffrey R. Jastrzab
Attorney, Agent, or Firm—Michael J. Jaro; Harold R. Patton

[57] ABSTRACT

A body implantable lead affixed with a pin or pins at its proximal end adapted to be connected to a pulse generator or signal detector with an electrode or electrodes at its distal end adapted to be placed within a body cavity or in contact with body tissue. One or more electrical conductors encased within nonconductive body compatible material electrically connects the electrode with a pin and comprises a length of resilient, single filar or multifilar coil conductor wherein the conductor is non-circular in cross section. The non-circular cross section is preferably elliptic, oval, rectangular or trapezoidal with a major dimension generally perpendicular to the longitudinal axis of the length of coiled conductor and its minor dimension generally parallel to that axis, whereby a specific ratio of torque to bending stiffness is effected. Preferably, the body implantable lead is a unipolar or a bipolar transvenous screw-in lead possessing a spiral shaped screw fixation mechanism at the distal end of the lead which is at least mechanically connected to said length of conductor. The proximal end of said length of conductor is electrically and mechanically connected to the connector pin. Rotation of the connector pin effects the rotation of the spiral attachment mechanism into body tissue.

18 Claims, 2 Drawing Sheets

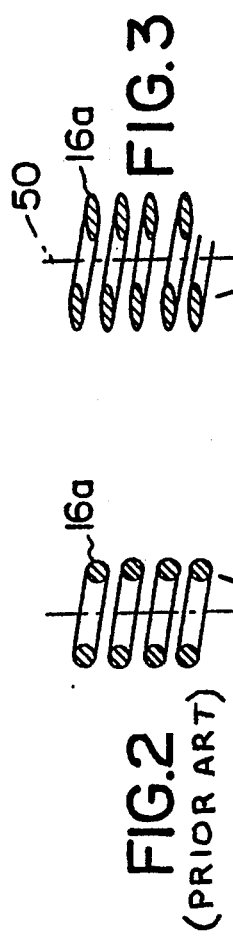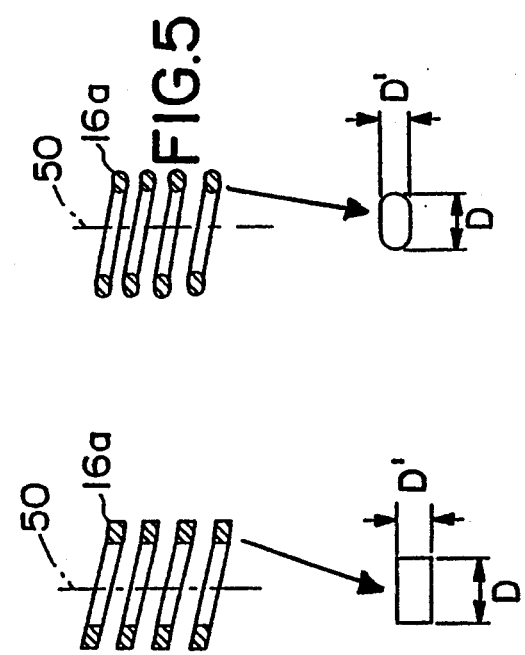
FIG.2 (PRIOR ART)
FIG.3
FIG.4
FIG.5
FIG.6

CONDUCTOR COIL WITH SPECIFIC RATIO OF TORQUE TO BENDING STIFFNESS

BACKGROUND OF THE INVENTION

This invention relates to an electrode or a lead which may be adapted to be connected to an electrical device and to contact a living organ to receive or conduct electrical signals therebetween. Notwithstanding its various uses, including applications in catheters and guide wires, this invention will be described as an endocardial pacing, and/or sensing lead for connecting a cardiac pacemaker and/or cardioverter/defibrillator pulse generator to cardiac tissue.

Body implantable cardiac pacemaker leads are quite well-known, their construction and function being described at length in medical journals during the past 25 years. The standard endocardial lead is of the type shown, for example, in U.S. Pat. No. 3,348,548, incorporated herein by reference, and comprises lengths of coiled wire conductors extending between a proximal pin(s) adapted to be connected to a pulse generator and a distal electrode(s) adapted to contact the endocardium of the heart. The lead is inserted and guided through a selected vein of the body until the distal end thereof is lodged in the apex of the right ventricle of the heart. A material, such as silicone rubber, or polyurethane, that is both electrical insulating and impervious to body fluids and tissue encases the coiled wire conductor either by a molding process or by insertion of the coiled wire conductor in a length of hollow silicone rubber, or polyurethane, tubing. In either case, a lumen extends down the center of the coiled wire conductor into which a stylet is advanced prior to insertion of the lead into the patient's vein to advance the lead through the patient's vein and to place the distal end of the lead bearing the electrode(s) at the desired position in the patient's heart.

Coiled wire conductor endocardial leads of the type disclosed in the aforementioned U.S. Pat. No. 3,348,548 employ a conductor that is circular in cross section. In more recent endocardial lead designs, multifilar conductors wound in parallel with a constant radius have been employed in order to use a smaller gauge conductor in order to, in turn, provide for a smaller diameter lead body which is both more flexible and more reliable than the single filar conductor described in the aforementioned U.S. Pat. No. 3,348,548.

Endocardial pacing leads have been categorized into passive or active fixation leads such as those shown, for example, by U.S. Pat. Nos. 3,902,501 and 4,106,512, respectively, each of which is herein incorporated by reference. The endocardial screw-in leads of the type shown in the aforementioned U.S. Pat. No. 4,106,512 employ the length of coiled wire conductor to transmit torque from the proximal connector end of the lead body to the distal fixation coil in order to advance that coil from the lead body and into heart tissue at a desired location within a chamber of the heart. In bipolar endocardial leads of the type described in the aforementioned U.S. Pat. No. 4,106,512, two conductor coils are coaxially arranged so that the inner coil may be rotated to rotate the fixation coil while the outer coil remains stationary. In this bipolar configuration, there are practical limits on the wire gauge which may be used to construct the inner coil inasmuch as it is required to transmit adequate torque to rotate the distal fixation mechanism.

Conductor coils from such wires with circular cross section have a fixed ratio between torque and bending stiffness. It is generally desirable to minimize the bending stiffness of the lead as a whole where that lead is provided with either a passive or active fixation mechanism to hold the distal electrode(s) in position within the heart. However, sufficient torque stiffness must be maintained to insure that the lead has adequate mechanical and handling characteristics. According to the present invention, the torque/bending stiffness ratio may be increased by using conductor coils wound with wires of non-circular cross section.

SUMMARY OF THE INVENTION

The above features and advantages of the present invention, as well as others, are accomplished by providing a body implantable, intravascular lead of the type having at least one electrically conductive pin at its proximal end adapted to be connected to a source of electrical energy and/or sensing circuit, and at least one electrode affixed to the distal end thereof, adapted to be firmly lodged in contact with body tissue, with an improvement in the construction of the lead comprising means for increasing torque control to effect the transmission of torque between the proximal and distal end of the lead without increasing lead bending stiffness through modification of the cross section of the wire from which the conductor is constructed.

In a preferred embodiment of the invention, the non-circular cross section of the conductor wire may be elliptical, rectangular, trapezoidal or oval as long as the dimension of the wire measured parallel to the coil axis (the minor dimension) is smaller than the dimension measured radially (the major dimension). The modification of the cross section of the wire causes the ratio between axial torque and radial bending stiffness to be modified so that the surface moment of inertia along or parallel to the coil axis exceeds the surface moment of inertia along a radial axis in the same coil. The coil thereby has a torque stiffness which is increased relatively to the bending stiffness.

The present invention may be utilized in passive or active fixation leads. This invention applies to screw-in leads with fixed screws or helifix type leads. Examples of a fixed screw-in electrode include Medtronic Model 5078 TM and Vitatron Helifix TM leads, as well as the fixed screw-in leads disclosed in U.S. Pat. No. 3,974,834, incorporated herein by reference.

In a preferred embodiment, the body implantable lead may take the form of a bipolar, endocardial, screw-in pacing lead having a pair of conductor coils arranged coaxially. The inner conductor coil is coupled at its proximal end to a connector pin and at its distal end to a corkscrew-shaped tissue penetrating active attachment mechanism, such as a helical coil. The inner conductor coil lies within an insulating sheath surrounded by the outer second conductor coil. The inner conductor coil is rotated by the rotation of the connector pin and in turn rotates the screw-in fixation mechanism. At least the first inner conductor coil which transmits the torque to the screw-in mechanism is constructed in the fashion described and claimed herein although it is also possible to construct the outer second conductor coil in the same or similar fashion.

Other features, advantages and objects of the present invention will hereinafter become more fully apparent from the following description of the drawings which illustrate preferred embodiments thereof.

BRIEF DESCRIPTION OF THE DRAWINGS

FIG. 2 shows in cross section a conventional circular wire coiled conductor;

FIG. 3 shows in cross section a first preferred embodiment of the coiled wire conductor; and FIGS. 4, 5 and 6 show in cross section further preferred embodiments of the coiled wire conductor of the present invention.

DESCRIPTION OF THE PREFERRED EMBODIMENTS

Figure 1:
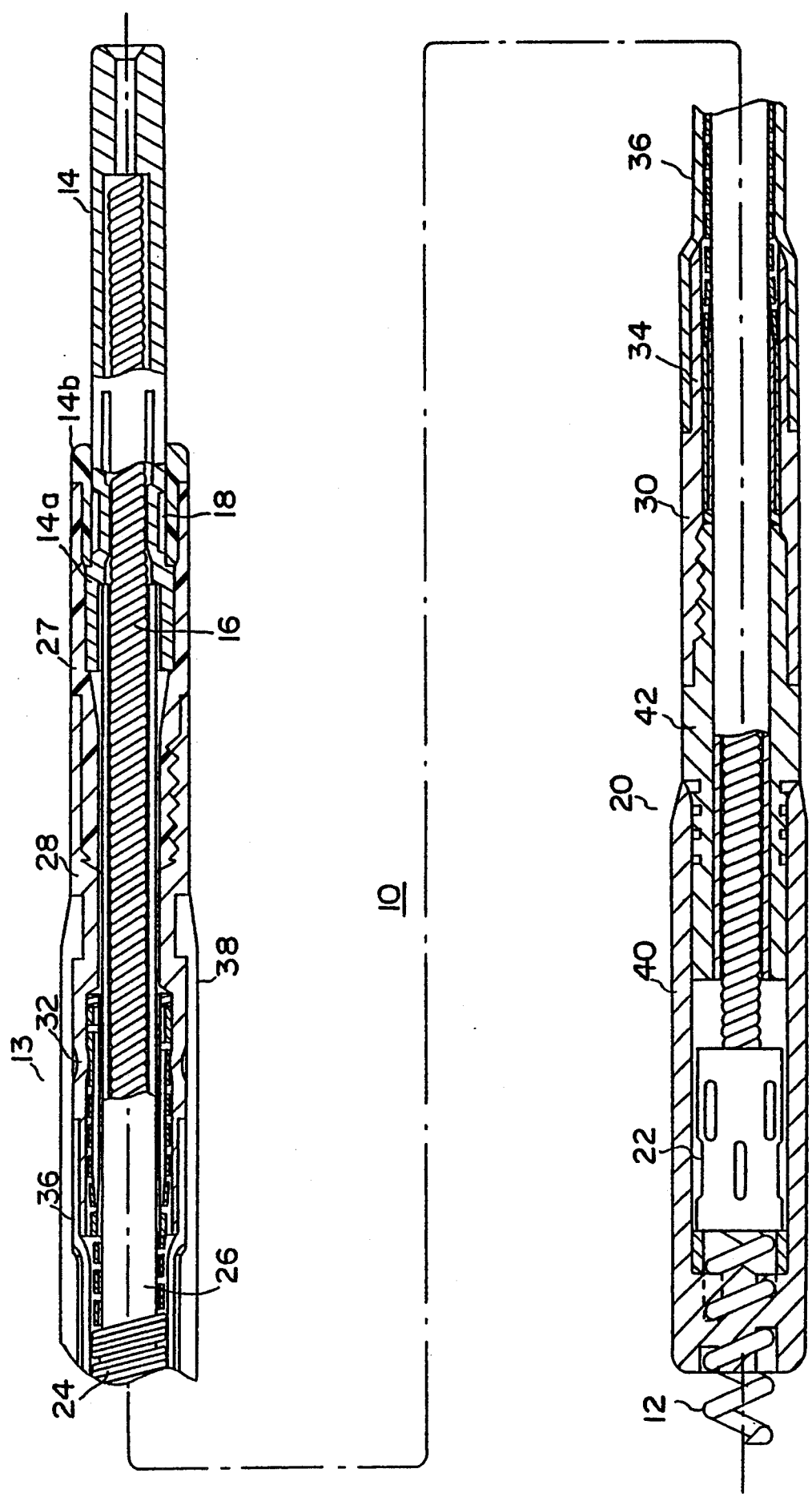
FIG. 1 shows a preferred embodiment of a bipolar version of the body implantable, intravascular lead of the present invention.

Referring now to the first preferred embodiment of the invention depicted in FIG. 1, there is shown a bipolar, coaxial, endocardial screw-in lead 10 and in particular the proximal and distal ends thereof.

The Medtronic Model 4016 TM endocardial, bipolar, screw-in lead, as shown in FIG. 1, is designed for pacing and sensing applications in either the atrium or the ventricle of the heart. The lead has application where permanent atrial, ventricular or dual chamber pacing system is indicated. The lead's tip electrode provides active fixation in the endocardium via a platinum-alloy helix. The helical screw-in electrode 12 can be extended or retracted by rotating the lead's connector pin 14 with a special fixation tool (not shown). This active fixation is particularly beneficial for patients who have smooth or hypertrophic hearts where lead dislodgement of a passive fixation lead may be a potential problem. An inner conductor coil 16 is mechanically and electrically coupled at swaging zone 18 to connector pin 14 at the proximal end 13 of the lead 10 and extends through the length of the lead body to the distal end 20 of the lead where it is mechanically and electrically connected by swaging ring 22 to helical screw-in electrode 12. The inner conductor coil 16 is multifilar, that is the coil constitutes two or more co-wound wires, as shown in FIG. 1 although it could be single filar.

A second, outer conductor coil 24 is arranged coaxially with the inner conductor coil 16 and insulated therefrom by an insulating sheath 26. The outer conductor coil 24 is similarly shown to be a multifilar coil although it too could be constructed of a single wire strand. The outer conductor coil 24 extends from the proximal connector ring 28 through the length of the lead 10 to terminate at the ring electrode 30 in the distal end 20 of the lead 10. Crimping zones 32 and 34 mechanically and electrically couple the proximal and distal ends of the outer conductor coil 24 to the connector ring 28 and ring electrode 30, respectively. A body compatible insulating tube 36 extends from the proximal end 13 of the lead 10 to the distal end 20 overlying the second outer conductor coil and is sealed at the respective ends to the connector ring 28 and ring electrode 30, respectively. At the proximal end 13, a second insulating tubular member 38 extends for a short distance over the crimping zone 32 and the proximal end of the insulating tube 36 to strengthen and seal the lead body and to provide a sealing arrangement with the pulse generator connector block.

At the distal end 20 of the lead, distal insulating sheath 40 and an insulating tubular member 42 retain the helical screw-in electrode 12 and ring electrode 30 in proper relationship to one another. The insulating sheath 40 encloses and supports the helical screw-in electrode 12 which is threaded through a corresponding helical passage in the distal end of insulating sheath 40. The insulating tubular member 42 joins the ring electrode 30 to the distal insulating sheath 40. The lead of FIG. 1 corresponds to the Medtronic Model 4016 TM endocardial, screw-in, bipolar, pacing lead which is illustrated and described in the article entitled "The Impact of Pending Technologies on a Universal Connector Standard" published in PACE, Nov.–Dec. 1986, Vol. 9, pp. 1186–1190.

The implantation of the lead through a vein and into a patient's heart is well-known to those of skill in the art. The lead is advanced transvenously until the distal end 20 is advanced into the atrium for atrial placement or in the right ventricle for ventricular placement. The lead is maneuvered under stylet control until the tip of the helical screw-in electrode 12 is positioned against either the desired atrial or ventricular endocardium. During the introduction and maneuvering of the lead, the helical screw-in electrode 12 and swaging ring 22 are retracted within the interior chamber of the insulating sheath 40. In order to fix the helical screw-in electrode 12 in position, the stylet guide (not shown) is removed from the connector pin 14 and rests against the stylet knob (not shown). An electrode fixation tool (not shown) is applied to the connector pin 14. While gently pressing the lead tip against the endocardium, the electrode fixation tool is rotated clockwise until the helical screw-in electrode 12 is completely exposed and screwed into the endocardial tissue which can be verified by fluoroscopy. Then the stylet, stylet guide and electrode fixation tool are removed, and the connector pin 14 is connected to the pacing pulse generator in a conventional fashion.

The connector pin 14 rotates at 14a, 14b with respect to the connector sheath 27 and rotates the inner conductor coil 16 to thereby advance the helical screw-in electrode 12 as described above. Thus the installation of the lead 10 requires the transmission of torque by the inner conductor coil 16. The necessity of transmitting adequate torque using a conventional circular coil conductor thus results in a certain minimum conductor coil gauge which, in turn, limits the overall flexibility of the lead. However, the lead must be very flexible for bending during pacing so that it easily follows the movements of the heart, valves and vessels. Thus, it is desirable to provide an endocardial pacing lead with a high strength and flexibility together with an overall small diameter, and to this end, the ratio of the torque to bending stiffness may be improved by altering the cross section of the coil conductor wire of leads of the type shown in FIG. 1.

FIG. 2 illustrates a typical prior art lead featuring coil conductor wire having a circular cross section. The present invention provides for an improved ratio of torque to bending stress through the use of non-circular cross section coil conductor wire as shown in FIGS. 3-6.

In FIG. 2, the circular cross section of the coil conductor 16a is shown to have a diameter D. For space wound coils existing of circular shaped wire of the prior art as shown in FIG. 2, a fixed relationship between spring constants (flexibility) for rotation and bending exists in the approximated relationship $$\frac{C_r}{C_b} = \frac{2+V}{2}$$

where $C_r$ is the spring constant for rotation, $C_b$ is the spring constant for bending and $V$ is the contraction modulus of the material of the coil. This relationship is independent from wire diameter and coil diameter.

The relationship between $C_r$ and $C_b$ may be varied by changing the shape of the wire cross section. FIG. 3 shows a coil made of a wire having an elliptic cross section. The elliptic shaped wire has a major dimension D perpendicular to the axis of the spaced wound coil 50 and a minor dimension D' measured parallel to the axis of the spaced wound coil. Minor dimension D' can be expressed as a fraction of diameter D where $D' = D \times \alpha$ and $\alpha$ is the fraction of the major diameter represented by the minor diameter, i.e., $\alpha = D'/D$. For this type of wire, the approximated relationship between $C_r$ and $C_b$ is $$\frac{C_r}{C_b} = \frac{1}{2}\left(\frac{2(1+V)}{1+\alpha^2} + \frac{1}{\alpha^2}\right)$$

Generally speaking, within the confines of the normal dimensions of the inner and outer coil diameters of the lead of FIG. 1, the coil becomes relatively stiffer for torque for $\alpha < 1$. Thus, it is possible to increase the torque/bending stiffness ratio ($C_r/C_b$) by altering the cross section of the coil conductor wire. The smaller the dimension D', the greater the torque/bending stiffness ratio.

FIGS. 4, 5 and 6 illustrate rectangular, oval and trapezoidal cross section wire wound in the same fashion as the wire of FIG. 3 so that the dimension D is greater than the dimension D' in each case. The relationship between $C_r$ and $C_b$ is the same as for the elliptical wire of FIG. 3. Other non-circular shapes which also act to increase coil stiffness without detrimentally imparting bend stiffness are also within the scope of the claimed invention and are readily apparent to those of skill in the art.

Altering the cross section of the coil conductor has several advantages. It is possible to increase torque control in a lead without increasing lead bending stiffness thus allowing one to optimize the handling characteristic of the lead. The torque stiffness can be increased while maintaining the bend stiffness. Alternatively, the bend stiffness can be decreased while maintaining torque stiffness. The improved torque/bending stiffness ratio will reduce material stress and increase the flex life of the lead. It will also reduce friction between coil and stylet, and between coil and tubing for coil rotation in a screw-in lead. Non-circular coil conductor wire also reduces longitudinal coil stiffness and thus friction in insulating sheath 40 when using screw-in leads.

It may also be desirable to have a lead or electrode with variable torque and stiffness properties. It will be apparent to those of skill in the art, for example, that a lead might have one type of space wound coil in the proximal portion and another in the distal portion and that the principles of this invention could be advantageously used to control the torque and stiffness properties in the two portions.

The present invention may also be applied in multilumen designs, where coils constructed in accordance with the present invention are placed in parallel rather than coaxially. In multilumen applications, the present invention will reduce longitudinal stiffness which leads to reduced bending stresses.

Although several embodiments of the invention have been illustrated in the accompanying drawings and described in the foregoing description of the preferred embodiments, it will be understood that the invention is not limited to the embodiments disclosed, but is capable of numerous rearrangements, modifications, and substitutions without departing from the scope of the invention.

By way of example, the present invention also has applications in catheters and guide wires for entering the coronary arteries. The improved torque/bending stiffness ratio of catheters and guide wires manufactured according to the present invention facilitates the control of the catheters and guide wires to be passed along the coronary arteries. The electrical aspects described above for leads, would not be relevant for applications of the present invention in catheters and guide wires.

What is claimed is:

1. A body-implantable, intravascular lead comprising:
   (a) a length of coiled conductor sheathed within a nonconductive body-compatible material wherein said conductor comprises a filar having a proximal end, a distal end a longitudinal axis and a non-circular cross-section, said cross-section having a major dimension generally perpendicular to the longitudinal axis of said length of coiled conductor and a minor dimension generally parallel to the longitudinal axis of said length of coiled conductor;
   (b) an electrode attached to said distal end of said length of coiled conductor; and
   (c) a connector pin attached to said proximal end of said coiled conductor.

2. A body-implantable, intravascular lead comprising:
   (a) a length of coiled conductor comprising a filar having a longitudinal axis and further having a proximal end and a distal end, said coiled conductor sheathed within a nonconductive body-compatible material;
   (b) an electrode connected to said distal end of said coiled conductor, said electrode having means for fixing said electrode with body tissue;
   (c) an electrically conductive connector pin coupled to said proximal end of said coiled conductor; and
   (d) said length of coiled conductor comprising a filar having a non-circular cross section, said cross section having a first dimension, measured generally parallel to the longitudinal axis of said coiled conductor, smaller than a second dimension, measured generally radially to the longitudinal axis of said coiled conductor.

3. The body-implantable, intravascular lead of claim 2 wherein said means for fixing said electrode with body tissue comprises a tissue penetrating helix.

4. The body-implantable, intravascular lead of claim 3 wherein said tissue penetrating helix means for fixing and removing said helix from tissue by rotation of said coiled conductor.

5. The body-implantable, intravascular lead of claim 2 wherein said coiled conductor is an inner coiled conductor and further comprising an outer coiled conductor arranged coaxially with said inner coiled conductor, said outer coiled conductor insulated from said inner coiled conductor by an insulating sheath.

6. The body-implantable, intravascular lead of claim 5 wherein said means for fixing said electrode with body tissue can be fixed or removed from tissue by rotation of said inner coiled conductor.

7. The body-implantable, intravascular lead of claim 1 or 2 wherein said coiled conductor has at least two filars.

8. The body-implantable, intravascular lead of claim 1 or 2 wherein said cross section of said coiled conductor is oval.

9. The body-implantable, intravascular lead of claim 1 or 2 wherein said cross section of said coiled conductor is elliptical.

10. The body-implantable, intravascular lead of claim 1 or 2 wherein said cross section of said coiled conductor is rectangular.

11. The body-implantable, intravascular lead of claim 1 or 2 wherein said cross section of said coiled conductor is trapezoidal.

12. A body-implantable, intravascular lead comprising:
   (a) a length of coiled conductor wire having a proximal end, a distal end and a coil axis wherein said conductor wire has a non-circular cross section, said cross section having a first dimension, measured generally parallel to said coil axis, smaller than a second dimension, measured generally radially to said coil axis;
   (b) an electrode attached to a distal end of said length of coiled conductor; and
   (c) a connector pin attached to said proximal end of said coiled conductor.

13. A body-implantable, intravascular lead comprising:
   (a) a length of coiled conductor wire having a proximal end, a distal end, a longitudinal axis and a radial axis, said coiled conductor wire having a non-circular cross section oriented in such a manner that the surface moment of inertia along said longitudinal axis exceeds the moment of inertia along said radial axis;
   (b) an electrode attached to a distal end of said length of coiled conductor; and
   (c) a connector pin attached to said proximal end of said coiled conductor.

14. The body-implantable, intravascular lead of claim 12 or 13 wherein said cross section of said coiled conductor wire is oval.

15. The body-implantable, intravascular lead of claim 12 or 13 wherein said cross section of said coiled conductor wire is elliptical.

16. The body-implantable, intravascular lead of claim 12 or 13 wherein said cross section of said coiled conductor wire is rectangular.

17. The body-implantable, intravascular lead of claim 12 or 13 wherein said cross section of said coiled conductor wire is trapezoidal.

18. The body implantable intravascular lead of claim 12 or 13 wherein said coiled conductor wire includes at least two filars.

* * * * *